United States Patent [19]

Albinson et al.

[11] Patent Number: 5,103,020

[45] Date of Patent: Apr. 7, 1992

[54] PREPARATION OF INDOLE DERIVATIVES

[75] Inventors: Frederick D. Albinson; John W. M. MacKinnon; Derek L. Crookes, all of Ware, England

[73] Assignee: Glaxo Group Limited, London, England

[21] Appl. No.: 717,940

[22] Filed: Jun. 20, 1991

[30] Foreign Application Priority Data

Jun. 21, 1990 [GB] United Kingdom ............... 9013845

[51] Int. Cl.$^5$ ................ C07D 209/16; C07D 209/04
[52] U.S. Cl. ................................. 548/504; 548/508
[58] Field of Search ............................. 548/504, 508

[56] References Cited

U.S. PATENT DOCUMENTS

| 4,816,470 | 3/1989 | Dowle et al. | 548/504 |
| 4,870,096 | 9/1989 | Oxford et al. | 548/503 |
| 5,037,845 | 8/1991 | Oxford | 548/504 |

OTHER PUBLICATIONS

Grandberg et al., *Khim. Geterotsikl. Soedin.*, 1974, Nr. 8, 1085 (translation).
CA 100:103175y Heterocyclic Compounds and Pharmaceuticals, Dowle et al., pp. 634–635, 1982.
CA 105:78831c 3-[2-(Dimethylamino)ethyl]-N-methyl-1H-indole-5-methanesulfonamide, Oxford, p. 637, 1984.

*Primary Examiner*—Mary C. Lee
*Assistant Examiner*—Joseph K. McKane
*Attorney, Agent, or Firm*—Bacon & Thomas

[57] ABSTRACT

A method for the preparation of 3-(2-aminoethyl)-N-methyl-1H-indole-5-methanesulphonamide by reaction of 4-hydrazino-N-methylbenzenemethanesulphonamide and 4-chloro-1-hydroxybutanesulphonic acid, sodium salt in the presence of an acid.

16 Claims, No Drawings

PREPARATION OF INDOLE DERIVATIVES

This invention relates to a process for the preparation of 3-(2-aminoethyl)-N-methyl-1H-indole-5-methanesulphonamide and physiologically acceptable salts and solvates thereof.

3-(2-Aminoethyl)-N-methyl-1H-indole-5-methanesulphonamide, which may be represented by the formula (I)

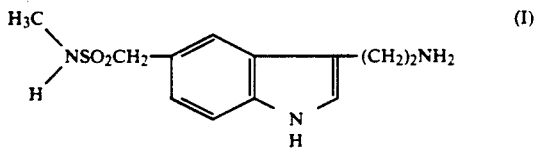

and its physiologically acceptable salts and solvates are discloses in UK Patent Specification No. 2124210. It exhibits selective vasoconstrictor activity and is indicated for use in the treatment of migraine. Compound (I) and its salts are also useful as intermediates for the preparation of 3-[2-(dimethylamino)ethyl]-N-methyl-1H-indole-5-methanesulphonamide which is described in UK Patent Specification No. 2165222.

UK Patent Specification No. 2124210 describes inter alia a method for preparing the compounds disclosed therein which comprises reacting an appropriate benzene hydrazine or a salt thereof with an appropriate aldehyde or a salt or a protected derivative thereof such as an acetal or a bisulphite addition complex. However, there is no specific disclosure of the use of a bisulphite addition complex in this reaction.

The preparation of tryptamine compounds from aryl hydrazines or salts thereof by reaction with both γ-halocarbonyl compounds and the corresponding bisulphite derivatives is described by Grandberg and Bobrova, Khim. Geterosikl Soedin., 1974, 1085. Grandberg states that, when salts of arylhydrazines are used, despite the variation of the conditions (change in temperature and of ratios of reagents) the yields of tryptamines are considerably less.

We have now surprisingly found that compound (I) can be prepared in good yield and high purity by cyclisation of the appropriate benzene hydrazine in association with an acid with a bisulphite addition complex of an appropriate aldehyde.

Thus the present invention provides a process for preparing compound (I) which comprises reacting a compound of formula (II)

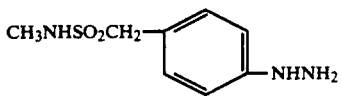

in association with an acid with a compound of formula (III)

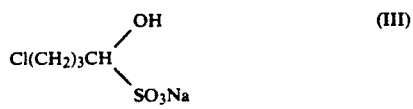

The present invention gives compound (I) in higher yield than when the free hydrazine is reacted with the bisulphite addition complex compound (III). Furthermore, the product is obtained directly as a crystalline solid suitable for use without further purification.

It will be appreciated that the relative amounts of compounds (II) and (III) used in the present invention may be varied. The reaction may conveniently be effected using 0.85 to 1.15 molar equivalents of compound (III) based upon compound (II) but preferably 1.0 to 1.1 molar equivalents of compound (III) will be used.

Any suitable acid may be employed in the reaction; suitable acids with which compound (II) may be associated include, for example, mineral acids, e.g. hydrochloric and sulphuric acids, and organic acids, e.g. trifluoroacetic acid. The acid is conveniently presented for use in the present invention by supplying compound (II) in the form of an acid addition salt, preferably as the hydrochloride salt. Conveniently the reaction is performed in the presence of about 0.8 to 1.2 equivalents based upon compound (II) of the mineral acid but preferably stoichiometric amounts of the acid are used.

The reaction is conveniently effected in a suitable reaction medium at elevated temperature, most conveniently at the reflux temperature of the reaction mixture. The reaction may conveniently be carried out under an inert gas atmosphere, for example under nitrogen.

Suitable reaction media which may be employed include aqueous alcohols such as methanol, ethanol, isopropanol or mixtures thereof. The alcohol:water ratio of the reaction medium is conveniently in the range 1:1 to 3:1 by volume, a preferred reaction medium being a mixture of industrial methylated spirits (IMS) and water in the ratio of 3:1 v/v.

In a particularly preferred embodiment of the present invention the reaction is effected in the presence of a pH modifying agent.

By the term pH modifying agent is meant an agent which has the effect of controlling the change in pH of the reaction mixture during the course of the reaction. Suitable agents include salts of weak acids such as salts of phosphoric, acetic, phthalic, carbonic and sulphurous acids, e.g. potassium dihydrogen phosphate, disodium hydrogen phosphate, trisodium phosphate, ammonium acetate, sodium acetate, potassium hydrogen phthalate, potassium carbonate, sodium hydrogen carbonate, sodium carbonate and sodium hydrogen sulphite. Where the reaction is effected in the presence of pH modifying agent, 0.1 to 1.0 molar equivalents of the said pH modifying agent based upon compound (II) will conveniently be used. Preferred pH modifying agents include salts of phosphoric acid, e.g. disodium hydrogen phosphate and trisodium phosphate. Preferably 0.1 to 0.35 molar equivalents of these pH modifying agents will be used. A particularly preferred pH modifying agent for use in the reaction is disodium hydrogen phosphate.

Where the reaction is performed in the presence of a pH modifying agent, the alcohol:water ratio of the reaction medium is suitably in the range 3:1 to 1:3 v/v.

According to a particularly preferred embodiment of the invention, compound (I) may be prepared by reacting compound (II) in the form of its hydrochloride salt with 1.0 to 1.1 molar equivalents of compound (III) in the presence of 0.25 equivalents of disodium hydrogen phosphate in a mixture of industrial methylated spirits (IMS) and water in the ratio 1:2.

The starting material of formula (II) is a known compound whose preparation is described in UK Patent Specification No. 2124210. Compound (III) is described by Grandberg et. al. as mentioned above.

Where it is desired to isolated compound (I) as a physiologically acceptable salt, this may be formed by conventional methods for example by treatment with an appropriate acid in a suitable solvent. Solvates of compound (I) may conveniently be prepared by crystallisation or recrystallization from an appropriate solvent.

The invention is further illustrated by the following non-limiting examples. All temperatures are in °C. IMS means industrial methylated spirit. HPLC means high performance liquid chromatography.

All the following examples relate to the preparation of 3-(2-aminoethyl)-N-methyl-1H-indole-5-methanesulphonamide, hereinafter Compound I.

EXAMPLE 1

(a) A mixture of 4-chloro-1-hydroxybutanesulphonic acid, sodium salt (4.27 g), 4-hydrazino-N-methylbenzenemethanesulphonamide (4.50 g), IMS (100 ml) and water (33 ml) was heated to reflux for 4.5 hours. Assay of the resulting solution by HPLC against a reference solution of the desired product indicated that the yield of Compound I in solution was 33.2% of theory based on the input hydrazine.

(b) A mixture of 4-chloro-1-hydroxybutanesulphonic acid, sodium salt (4.27 g), 4-hydrazino-N-methylbenzenemethanesulphonamide (4.50 g), 2M-hydrochloric acid (10 ml, 1.0 equivalent with respect to the hydrazine), disodium hydrogen phosphate (705 mg), IMS (100 ml) and water (33 ml) was heated to reflux for 4.5 hours. Assay of the resulting solution by HPLC against a reference solution indicated that the yield of Compound I in solution was 57.3% of theory based on the input hydrazine.

(c) A mixture of 4-chloro-1-hydroxybutanesulphonic acid, sodium salt (4.27 g), 4-hydrazino-N-methylbenzenemethanesulphonamide hydrochloride (5.05 g, equivalent to 4.50 g of the free base), disodium hydrogen phosphate (705 mg), IMS (100 ml) and water (33 ml) was heated to reflux for 4.5 hours. Assay of the resulting solution by HPLC against a reference solution indicated that the yield of Compound I in solution was 67.0% of theory based on the input hydrazine hydrochloride.

EXAMPLE 2

(a) A mixture of 4-chloro-1-hydroxybutanesulphonic acid, sodium salt (8.7 g), 4-hydrazino-N-methylbenzenemethylsulphonamide hydrochloride (10.0 g), filter aid (1.5 g), IMS (90 ml) and water (180 ml) was heated to reflux for 4.5 hours. Assay of the resulting solution by HPLC against a reference solution of the desired product indicated that the yield of Compound I in solution was 53.4% of theory based on the input hydrazine hydrochloride.

(b) The above experiment was repeated with potassium carbonate (1.65 g) added. The measure yield of Compound I in solution was 55.2% of theory based on the input hydrazine hydrochloride.

(c) Experiment (a) was repeated with disodium hydrogen phosphate (1.41 g) added. The measured yield of Compound I in solution was 70.5% of theory based on the input hydrazine hydrochloride.

EXAMPLE 3

(a) A mixture of 4-chloro-1-hydroxybutanesulphonic acid, sodium salt (4.27 g), 4-hydrazine-N-methylbenzenemethanesulphonamide hydrochloride (5.05 g), disodium hydrogen phosphate (705 mg), methanol (66 ml) and water (66 ml) was heated to reflux for 4.5 hours. Assay of the resulting solution by HPLC against a reference solution of the desired product indicated that the yield of Compound I in solution was 70.5% of theory based on the input hydrazine hydrochloride.

(b) The above experiment was repeated except that a mixture of propan-2-ol (53 ml) and water (80 ml) was used as solvent. The measured yield of Compound I in solution was 68.7% of theory based on input hydrazine hydrochloride.

EXAMPLE 4

A mixture of 4-chloro-1-hydroxybutanesulphonic acid, sodium salt (539 g), 4-hydrazino-N-methylbenzenemethanesulphonamide hydrochloride (606 g), disodium hydrogen phosphate (84.7 g), IMS (12.0 liters) and water (4.0 liters) was heated at reflux under nitrogen for 4.5 hours. The mixture was concentrated by distillation at atmospheric pressure, water (5.4 liters) and filter-aid (90 g) were added, and distillation was continued under reduced pressure. The concentrate was treated with dichloromethane (6.0 liters) and potassium carbonate (108 g), and the resulting mixture was filtered. The aqueous phase of the filtrate was washed with dichloromethane (3×6.0 liters) and was then treated successively with dichloromethane (4.2 liters), IMS (1.8 liters), and a solution of potassium carbonate (5.4 kg) in water (4.8 liters). The mixture was stirred, and the layers separated.

Exactly one half of the organic layer was decolourised by stirring with activated charcoal, concentrated by distillation at atmospheric pressure, seeded with product and allowed to cool to room temperature. Isopropyl acetate (2.25 liters) was added and the suspension was maintained at room temperature overnight. The solid was filtered off, washed with isopropyl acetate and dried to give Compound I as a fawn solid (180 g, 56% of theory) identical with authentic material described in UK Patent Specification No. 2124210.

EXAMPLE 5

A mixture of 4-chloro-1-hydroxybutanesulphonic acid, sodium salt (43.9 g), 4-hydrazino-N-methylbenzenemethanesulphonamide hydrochloride (50 g), disodium hydrogen phosphate (7.1 g), filter aid (7.5 g), IMS (450 ml) and water (900 ml) was heated at reflux under nitrogen for 4.5 hours. The mixture was concentrated by distillation at atmospheric pressure until about 300 ml of distillate was collected then distillation was continued under reduced pressure. The concentrate was treated with a 17.5% w/v solution of potassium carbonate (52.2 ml) and the resulting mixture was filtered. The filtrate was washed with dichloromethane (2×470 ml) and was then treated successively with dichloromethane (260 ml) and IMS (14.5 ml). The mixture was stirred and treated successively with a solution of sodium hydroxide (11.3 g) in water (12.7 ml) and sodium chloride (135 g). After stirring for one hour at room temperature the solid was filtered off, washed with water and dried to give compound 1 as a fawn solid (33.7 g, 63.5% of theory) identical with authentic material described in UK patent specification no. 2124210.

We claim:
1. A process for the preparation of a compound of formula (I)

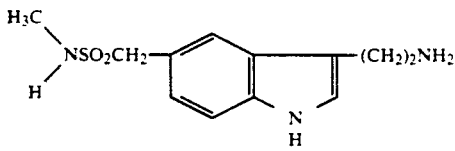

which comprises reacting a compound of formula (II)

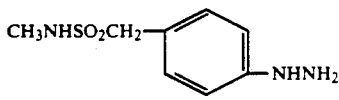

in association with an acid with a compound of formula (III)

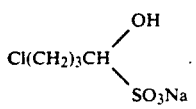

2. A process as claimed in claim 1 wherein compound (III) is present in an amount of 0.85 to 1.15 molar equivalents of compound (II).

3. A process as claimed in claim 2 where 1.0 to 1.1 molar equivalents of compound (III) are present.

4. A process as claimed in claim 1 wherein the acid is selected from hydrochloric, sulphuric and trifluoroacetic acids.

5. A process as claimed in claim 4 wherein the acid is hydrochloric acid.

6. A process as claimed in claim 1 wherein the acid is present in an amount of from 0.8 to 1.2 molar equivalents of the compound of formula (II).

7. A process as claimed in claim 6 where the acid is present in an amount of 1 molar equivalent.

8. A process as claimed in claim 1 when the reaction is carried out in a solvent system comprising an aqueous alcohol.

9. A process according to claim 8 wherein the alcohol is ethanol or industrial methylated spirit.

10. A process according to claim 9 wherein the ratio of alcohol to water is in the range of 1:3 to 3:1.

11. A process as claimed in claim 1 wherein a pH modifying agent is also present in the reaction mixture.

12. A process as claimed in claim 11 wherein the pH modifier is selected from a salt of phosphoric, acetic, phthalic, carbonic and sulphurous acids.

13. A process as claimed in claim 11 wherein the pH modifier is a salt of phosphoric acid.

14. A process as claimed in claim 11 wherein the pH modifier is present in an amount of 0.1 to 0.35 molar equivalents of compound (II).

15. A process as claimed in claim 11 wherein the pH modifying agent is disodium hydrogen phosphate.

16. A method for the preparation of a compound of formula (I)

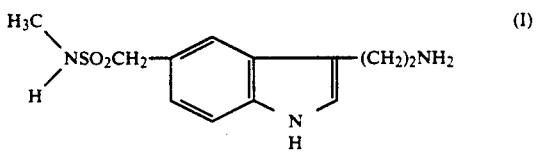

which comprises reacting the hydrochloride salt of a compound of formula (II)

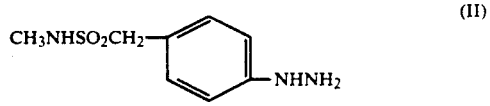

a compound of formula (III)

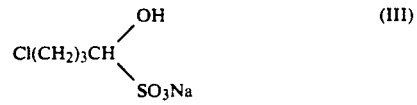

and disodium hydrogen phosphate in a molar ratio of 1:1.0 to 1.1:0.25 in a solvent system comprising industrial methylated spirit and water in a ratio of 1:2 by volume.

* * * * *